United States Patent [19]

Janssen et al.

[11] Patent Number: 4,670,454
[45] Date of Patent: Jun. 2, 1987

[54] AZOLYLMETHYLCYCLOALKANES, THEIR PREPARATION AND THEIR USE AS DRUGS

[75] Inventors: Bernd Janssen, Ludwigshafen; Norbert Meyer, Ladenburg; Ernst-Heinrich Pommer, Limburgerhof; Eberhard Ammermann, Ludwigshafen; Friedrich-Wilhelm Kohlmann, Moorrege; Walter Wesenberg, Bujendorf ueber Eutin; Wolfgang Heberle, Starnberg, all of Fed. Rep. of Germany

[73] Assignee: BASF Aktiengesellschaft, Fed. Rep. of Germany

[21] Appl. No.: 584,866

[22] Filed: Feb. 29, 1984

[30] Foreign Application Priority Data

Mar. 3, 1983 [DE] Fed. Rep. of Germany ....... 3307477
Mar. 3, 1983 [DE] Fed. Rep. of Germany ....... 3307479

[51] Int. Cl.$^4$ .................. C07D 249/08; C07D 233/56; A61K 31/41; A61K 31/415
[52] U.S. Cl. ..................... 514/383; 514/396; 514/397; 514/184; 548/101; 548/262; 548/335; 548/336; 548/341; 546/283; 549/472; 549/59
[58] Field of Search ............... 548/101, 262, 341, 336, 548/335; 424/245, 269, 273 R; 546/283

[56] References Cited

U.S. PATENT DOCUMENTS

| | | | |
|---|---|---|---|
| 4,183,940 | 1/1980 | Buchel et al. | 548/262 |
| 4,284,641 | 8/1981 | Thorogood | 514/396 |
| 4,317,830 | 3/1982 | Thorogood | 514/396 |
| 4,522,948 | 6/1985 | Walker . | |

FOREIGN PATENT DOCUMENTS

| | | | |
|---|---|---|---|
| 867245 | 11/1978 | Belgium | 548/262 |
| 2855329 | 7/1980 | Fed. Rep. of Germany | 514/396 |
| 2249616 | 5/1975 | France | 548/341 |
| 1464224 | 2/1977 | United Kingdom | 548/262 |
| 1594859 | 8/1981 | United Kingdom | 548/262 |

Primary Examiner—Glennon H. Hollrah
Assistant Examiner—D. Dinner
Attorney, Agent, or Firm—Keil & Weinkauf

[57] ABSTRACT

Azolylmethylcycloalkanes of the formula I

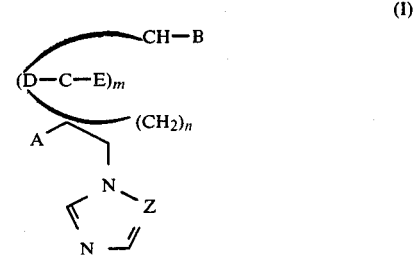

where A and B are identical or different and are each hydrogen, unsubstituted or halogen-substituted alkyl of 1 to 4 carbon atoms, naphthyl, hetaryl, biphenyl or phenyl, where the phenyl radical can be substituted by halogen, nitro, alkyl, alkoxy or haloalkyl, each of 1 to 4 carbon atoms, phenoxy or phenylsulfenyl, D and E are identical or different and are each hydrogen or halogen, Z is CH or N, m can be 1, 2, 3 or 4 and n can be 0, 1 or 2, their addition salts with acids and their metal complexes, and the preparation of these compounds, are described. The compounds are useful for treating disorders and for crop, wood and material protection.

7 Claims, No Drawings

AZOLYLMETHYLCYCLOALKANES, THEIR PREPARATION AND THEIR USE AS DRUGS

The present invention relates to novel azolylmethylcycloalkanes, processes for their preparation and agents which contain these compounds and can be used as antimycotics and fungicides, as well as their use for treating disorders.

A large number of antimycotic agents, eg. azolylmethylcarbinols, such as miconazole (German Laid-Open Application No. DOS 1,940,388), or azolylmethyldioxolanes, such as ketoconazole (German Laid-Open Application No. DOS 2,804,096), are known, but their actions are not always satisfactory (Chemotherapy 22 (1976), 1; Dtsch. Apoth. Ztg. 118 (1978), 1269; Z. Hautkr. 56 (1981), 1109; Am. Rev. Respir. Dis. 126 (1982), 171; and Selecta 49 (1982), 4602. Furthermore, the use of azole compounds, such as azolylmethylcarbinols or azolylmethylketones (German Laid-Open Application No. DOS 2,431,407 and French Patent No. 2,249,616), as fungicides has been disclosed. However, their action is unsatisfactory.

It is an object of the present invention to provide novel compounds which have a better antimycotic and fungicidal action.

We have found that this object is achieved, and that azolylmethylcycloalkanes of the formula I

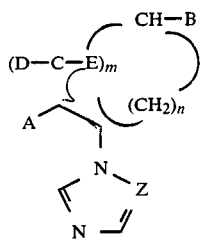

(I)

where A and B are identical or different and are each hydrogen, unsubstituted or halogen-substituted alkyl of 1 to 4 carbon atoms, naphthyl, hetaryl, biphenyl or phenyl, where the phenyl radical can be substituted by halogen, nitro, alkyl, alkoxy or haloalkyl, each of 1 to 4 carbon atoms, phenoxy or phenylsulfenyl, D and E are identical or different and are each hydrogen or halogen, Z is CH or N, m can be 1, 2, 3 or 4 and n can be 0, 1 or 2, their tolerated addition salts with acids and their metal complexes have good antimicrobial properties, in particular antimycotic and fungicidal properties.

The novel compounds of the formula I contain chiral centers and are generally obtained in the form of racemates. While the novel azolylmethylcyclopropanes of the formula I, where m is 1, n is 0 and neither A nor B is H, can be synthesized diastereoselectively by a simple procedure, in general mixtures of the erythro and threo forms are obtained. In this case, the diastereomer of the novel compounds can be separated by, for example, solubility differences or column chromatography, and can be isolated in the pure form. From the pure diastereomer pairs, it is possible to obtain pure enantiomers by a conventional method. Both these and their mixtures (racemates) are embraced by the present invention. To prepare antimicrobial or fungicidal agents, either the pure diastereomers or enantiomers or their mixtures can be used.

A and B are each, for example, hydrogen, methyl, ethyl, propyl, isopropyl, butyl, sec.-butyl, isobutyl, tert.-butyl, trifluoromethyl, 1-naphthyl, 2-naphthyl, p-biphenyl, phenyl, 2-chlorophenyl, 3-chlorophenyl, 4-chlorophenyl, 4-fluorophenyl, 4-bromophenyl, 2,4-dichlorophenyl, 3,4-dichlorophenyl, 3,5-dichlorophenyl, 2,6-dichlorophenyl, 3-chloro-4-methylphenyl, 2-methoxyphenyl, 3-methoxyphenyl, 2,4-dimethoxyphenyl, 3,4-dimethoxyphenyl, 4-methoxyphenyl, 4-ethoxyphenyl, 4-tert.-butoxyphenyl, 4-methylphenyl, 4-ethylphenyl, 4-isopropylphenyl, 4-tert.-butylphenyl, 4-phenoxyphenyl, 3-phenoxyphenyl, 3-nitrophenyl, 4-nitrophenyl, 3-trifluoromethylphenyl, 4-trifluoromethylphenyl, 4-phenylsulfenylphenyl, 3-furanyl, 2-furanyl, 3-thienyl, 2-thienyl, 2-pyridyl, 3-pyridyl or 4-pyridyl.

D and E are each, for example, fluorine, chlorine, bromine or, preferably, hydrogen.

When the novel substances are used as antimycotics, preferred acids for the formation of physiologically tolerated salts are hydrohalic acids, eg. hydrobromic acid and in particular hydrochloric acid, with which the novel compounds form salts which crystallize particularly readily. Other examples are phosphoric acid, nitric acid, sulfuric acid, monofunctional and bifunctional carboxylic acids and hydroxycarboxylic acids, eg. acetic acid, oxalic acid, maleic acid, succinic acid, fumaric acid, tartaric acid, citric acid, salicyclic acid, sorbic acid or lactic acid, and sulfonic acids, eg. p-toluenesulfonic acid and naphthalene-1,5-disulfonic acid.

Examples of acid addition salts which are suitable for use as fungicides are the hydrochlorides, bromides, sulfates, nitrates, phosphates, oxalates and dodecylbenzenesulfonates. The activity on the salts is attributable to the cation, so that any desired anion may be chosen. For practical reasons, however, non-phytotoxic anions are used.

The salts are prepared by reacting an azolylmethylcycloalkane with an appropriate acid.

Metal complexes which can be used in fungicides are those obtained from a compound of the formula I and a salt of a metal, for example of copper, zinc, tin, manganese, iron, cobalt or nickel, with an inorganic acid, eg. hydrochloric acid, sulfuric acid, phosphoric acid or hydrobromic acid. The metal complexes are prepared by reacting an azolylmethylcycloalkane with an appropriate metal salt.

The novel antimicrobial compounds of the formula I can be prepared by a process in which (a) a cycloalkane of the formula II

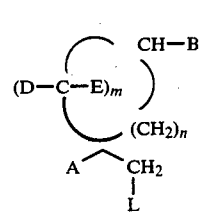

(II)

where A, B, D, E, m and n have the above meanings and L is a leaving group which can be substituted nucleophilically, is reacted with a compound of the formula III

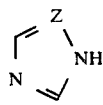
(III)

where Z has the above meanings, or (b) a compound of the formula II, where A, B, D, m and n have the above meanings and L is a hydroxyl group, is reacted with a compound of the formula IV

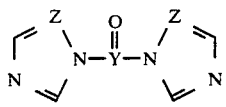
(IV)

where Z has the above meanings and Y is carbon or sulfur, in an aprotic solvent, and the resulting compound is, if desired, converted to its physiologically tolerated addition salts with acids.

Reaction (a) is preferably carried out in the presence or absence of a solvent or diluent and with or without the addition of an inorganic or organic base or of a reaction accelerator at from 10° to 120° C. Preferred solvents and diluents include ketons, eg. acetone, methyl ethyl ketone or cyclohexanone, nitriles, eg. acetonitrile, esters, eg. ethyl acetate, ethers, eg. diethyl ether, tetrahydrofuran or dioxane, sulfoxides, eg. dimethyl sulfoxide, amides, eg. dimethylformamide, dimethylacetamide or N-methylpyrrolidone, and sulfolane, as well as mixtures of these.

Examples of suitable bases, which may also be used as acid acceptors in the reaction, are alkali metal hydroxides, such as lithium hydroxide, sodium hydroxide or potassium hydroxide, alkali metal carbonates, such as sodium carbonate, potassium carbonate, sodium bicarbonate or potassium bicarbonate, or an excess of 1,2,4-triazole, imidazole, pyridine or 4-dimethylaminopyridine. However, other conventional bases may also be used Preferred reaction accelerators are metal halides, eg. sodium iodide or potassium iodide, quaternary ammonium salts, eg. tetrabutylammonium chloride, bromide or iodide or benzyltriethylammonium chloride or bromide, and crown ethers, eg. 12-crown-4, 15-crown-5, 18-crown-6, dibenzo-18-crown-6 or dicyclohexanone-18-crown-6.

The reactions are carried out in general at from 10° to 120° C., under atmospheric or superatmospheric pressure, continuously or batchwise.

Reaction (a) can also be carried out as follows: the compound III is converted to a metal salt, preferably an alkali metal salt, and this is reacted with a compound II in the presence or absence of a solvent or diluent and with or without the addition of a strong inorganic or organic base or of a reaction accelerator, at from −10° to +120°. Preferred solvents or diluents include amides, such as dimethylformamide, diethylformamide, dimethylacetamide, diethylacetamide, N-methylpyrrolidone and hexamethylphosphorotriamide, sulfoxides, eg. dimethyl sulfoxide, and finally sulfolane.

Examples of suitable bases, which may also be used as acid acceptors in the reaction, are alkali metal hydrides, which as lithium hydride, sodium hydride or potassium hydride, alkali metal amides, such as sodium amide or potassium amide, and sodium tert.-butoxide, potassium tert.-butoxide, lithium-triphenylmethyl, sodium-triphenylmethyl, potassium-triphenylmethyl, naphthalene-lithium, naphthalene-sodium and naphthalene-potassium.

Preferred reaction accelerators are metal halides, eg. sodium iodide or potassium iodide, quaternary ammonium salts, eg. tetrabutylammonium chloride, bromide or iodide or benzyltriethylammonium chloride or bromide, and crown ethers, eg. 12-crown-4, 15-crown-5, 18-crown-6, dibenzo-18-crown-6 or dicyclohexanone-18-crown-6.

Suitable solvents or diluents for reaction (b) are polar organic solvents, such as nirilies, eg. acetonitrile, sulfoxides, eg. dimethyl sulfoxide, formamides, eg. dimethylformamide, ketones, eg. acetone, ethers, eg. diethyl ether or tetrahydrofuran, and in particular chlorohydrocarbons, eg. methylene chloride nd chloroform.

The reaction is carried out in general at from 0° to 100° C., preferably from 20° to 80° C. Where a solvent is present, the reaction is advantageously carried out at the boiling point of the particular solvent.

In carrying out process (b), about 1 mole of carbonyl-bis(1-(1,2,4-triazole)) or carbonyl-bis(1-imidazole) or preferably about 1 mole of sulfonyl-bis(1-(1,2,4-triazole)) or sulfonyl-bis(1-imidazole) is employed per mole of the compound of the formula II where L is OH, or the stated sulfonyl compound is produced in situ.

The resulting compounds of the formula I are isolated by a conventional method, purified if required and, if desired, converted with an acid to a salt, or with a metal salt to a complex.

The starting compounds of the formula II are obtainable by the following routes: The compounds of the formula II, in which L is a leaving group which can be substituted nucleophilically, can be prepared, using a method of synthesis which is known in principle, by reacting a compound of the formula II where L is OH with a halide carrier, such as hydrogen chloride, hydrogen bromide, thionyl chloride, thionyl bromide, acetyl bromide, phosphorus tribromide or the phenylphosphine-bromine complex or sulfonyl chlorides, such as methane-, trifluoromethane-, nonafluorobutane-, 2,2,2-trifluoroethane-, 4-methylbenzene-, 4-bromobenzene-, 4-nitrobenzene- or benzenesulfonyl chloride, in the presence or absence of an inert solvent and of an organic or inorganic base, where the latter may also serve as the solvent (Houben-Weyl-Müller, Methoden der organischen Chemie, Vol. 5/3, Stuttgart 1964, page 760 et seq.; Vol. 5/4, Stuttgart 1960, page 354 et seq.; Vol. 9, Stuttgart 1955, pages 388 and 663; and J. org. Chem. 35 (1970), 3195).

Hydroxymethylcycloalkanes of the formula II where L is OH are obtained in accordance with the following diagram:

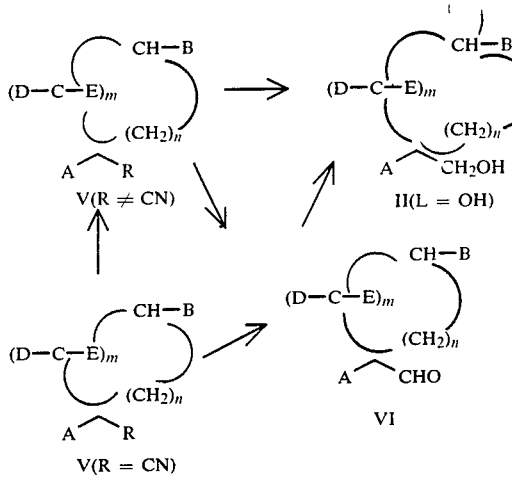

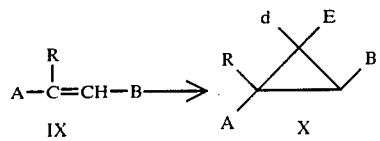

Nitriles of the formula V where R is CN can be subjected to solvolysis under acidic or alkaline conditions at from 20° to 120° C. in the presence of a solvent to give the corresponding carboxylic acid derivatives V in which R is not CN, these being converted by a conventional method to the alcohols II, where L is OH, by reduction with a complex hydride, eg. lithium aluminum hydride or sodium borohydride, in the case of an anhydride, or with hydrogen in the presence of a catalyst, under atmospheric or superatmospheric pressure, by a multistage (V→VI→II) or single-stage procedure.

The nitrile V in which R is CN can be reduced with diisobutyl aluminum hydride (Synthesis 1975, 617) to the aldehyde VI, which can be further reduced with a complex hydride, eg. sodium borohydride or lithium aluminum hydride, or with hydrogen in the presence of a catalyst to give the alcohol II in which L is OH.

The cycloalkylcarboxylic acid derivatives V, in which D and E are each hydrogen, are prepared by a conventional method, by bisalkylation of a carboxylic acid derivative VII with a bifunctional compound VIII, in which L is a leaving group which can be substituted nucleophilically.

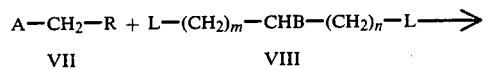

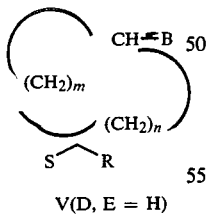

This reaction is preferably carried out under phase-transfer conditions (Rocz. Chem. 40 (1966), 1647 and Przen. Chem. 46 (1967), 393), but can also be carried out in the presence of a strong base, for example a metal hydride or metal amide (J. Amer. Chem Soc. 69 (1947), 2902). Cyclopropyl derivatives of the formula X, where A and B have the above meanings, R is a nitrile or ester group or an aldehyde group which may or may not be acetalized and D and E are each hydrogen, may furthermore preferably be obtained by cyclopropanation of α,β-unsaturated nitriles or aldehyde or carboxylic acid derivatives of the formula IX, where A, B and R have the above meanings.

Trimethylsulfoxonium salts are particularly suitable for the reaction, these being reacted with an α,β-unsaturated carboxylic acid derivative IX in an inert solvent in the presence of a strong base, for example an alkali metal alcoholate, such as potassium tert.-butylate. If a stereochemically pure olefin IX is used as the starting material, the pure diastereomeric cyclopropane is obtained (Z. Naturforsch. 18 [b] (1976), 976; and Chem. Ber. 98 (1965), 3721. Other processes for the preparation of cyclopropanes by intramolecular reaction or by reaction of olefins with reagents which transfer methylene groups, eg. diazomethane, or by the Simmons-Smith method have been described (Houben-Weyl-Müller, Methoden der organischen Chemie, Stuttgart 1971, Vol. 4/3, pages 32–148).

Cyclopropyl derivatives of the formula X, where A and B have the above meanings, R is a nitrile or ester group or an aldehyde group which may or may not be acetalized, and D and E independently of one another are each hydrogen or halogen, with the exception of those compounds in which D and E are simultaneously hydrogen, are obtained by reacting an α,β-unsaturated aldehyde or carboxylic acid derivative IX with a mono- or dihalocarbene, which as a rule is produced in situ by well-known processes (cf. for example Houben-Weyl-Müller, Methoden der organischen Chemie, Stuttgart 1971, Vol. 4/3, page 150 et seq.) or by a reaction carried out under phase-transfer catalyst (Liebigs Ann. 758 (1972), 148; Synth. Commun. 3 (1973), 305; and Tetrahedron 33 (1977), 363).

Surprisingly, the novel azole derivatives, in addition to good antibacterial and antimycotic in vitro activity, exhibit a better, therapeutically useful in vivo activity, in particular against dermatophytes and Candida, than conventional preparations. The active compounds according to the invention hence constitute a valuable enrichment of pharmacy.

The action against dermatophytes, bacteria and protozoa can be demonstrated by conventional methods as described in, for example, P. Klein, Bakteriologische Grundlagen der chemotherapeutischen Laboratoriumspraxis, Springer-Verlag Berlin, 1957. The surprising action against yeasts was demonstrated in the pseudomycelium and mycelium phase test, using Candida albicans (German Laid-Open Application No. DOS 3,010,093). The minimum inhibitory concentrations (MIC) reached in the agar dilution test were examined.

For a large number of the states examples, these concentrations are from 0.5 to 16 µg/ml against dermatophytes, and from 0.0078 to 1 µg/ml against parasitic yeasts in the pseudomycelium and mycelium phase test. Even against a number of molds, the MIC values are from 0.25 to 16 µg/ml.

In the case of bacteria, inhibitory values of from 1 to 64 µg/ml were found.

Therapeutic trials on animals showed that, after oral administration, azole derivatives according to the invention were highly effective against systemic infections by fungi and yeasts, or local infections, for example *Candida vaginitis* of the rat, and were superior to the reference substance ketoconazole. In the case of local treatment of *Candida vaginitis* of the rat, small doses of the azole derivatives described here were sufficient for complete cure. With standard antimycotics, eg. clotrimazole, miconazole, etc., larger amounts of substance were always required for the same period of treatment.

Trichophytosis infections in the guinea-pig could be cured by local treatment with small doses.

The compounds can be used alone or together with other conventional active compounds, in particular antibiotics.

The chemotherapeutic agents or formulations containing conventional solid, semi-solid or liquid excipients or diluents and the conventionally used pharmaceutical auxiliaries, according to the desired route of administration, and with a dose suitable for use, are prepared in a conventional manner, in particular by mixing (cf. H. Sucker et al., Pharmazeutische Technologie, Thieme-Verlag, Stuttgart, 1978).

Examples of suitable forms for administration are tablets, coated tablets, capsules, pills, aqueous solutions, suspensions and emulsions, sterile or non-sterile injectable solutions, non-aqueous emulsions, suspensions and solutions, ointments, creams, pastes, lotions, etc.

The therapeutic compound is present in pharmaceutical formulations preferably in a concentration of from 0.5 to 90% by weight, based on the total mixture.

In the case of oral administration, in both human and veterinary medicine, the active compound or compounds can be administered in general in amounts of from about 1.0 to about 10.0, preferably from 2 to 6, mg/kg of body weight per day, preferably in the form of several individual administrations, in order to achieve the desired results. However, it may be necessary to deviate from the stated doses, and to do so as a function of the nature and severity of the illness, the type of formulation and the route of administration of the drug, as well as the period or interval over which the administration is effected. Hence, it may be sufficient in some cases to use less than the abovementioned amount of active compounds, whereas in other cases the stated amount of active compound has to be exceeded.

The novel compounds not only are active against fungi which are pathogenic to humans, but can also be used as fungicides in agriculture.

They, and their salts and metal complex compounds, have an excellent action on a board spectrum of plant-pathogenic fungi, especially from the Ascomycetes and Basidiomycetes classes. Some of them have a systemic action and may be used as soil and foliar fungicides.

The fungicidal compounds are of particular interest for combating a large number of fungi in various crops or their seed, especially wheat, rye, barley, oats, rice, Indian corn, cotton, soybeans, coffee, sugarcane, fruit, ornamentals in horticulture, and vegetables, such as cucumbers, beans and Cucurbitaceae.

The novel compounds are particularly suitable for combating the following diseases: *Erysiphe graminis* in cereals, *Erysiphe cichoriacearum* in Cucurbitaceae, *Podosphaera leucotricha* in applies, *Uncinula necator* in grapes, Puccinia species in cereals, *Rhizoctonia solani* in cotton, Ustilago species in cereals and sugarcane, *Venturia inaequalis* (apple scab), *Septoria nodorum* in wheat, *Botrytis cinerea* in grapes and strawberries, *Cercospora musae* in bananas, *Pseudocercosporella herpotrichoides* in wheat and barley, *Hemileia vastatrix* in coffee, and *Piricularia oryzae* in rice.

The compounds are applied by spraying or dusting the plants, or treating the seed with the active ingredients. Application may be effected before or after infection of the plants or seed by the fungi.

The novel active ingredients can be converted into the conventional formulations, e.g. solutions, emulsions, suspensions, dusts, powders, pastes and granules. The form of application depends entirely on the purpose for which the agent is to be used; at all events, it should ensure a fine and uniform distribution of the active ingredients. The formulations are prepared in the conventional manner, for example by diluting the active ingredient with solvents and/or carriers, with or without the addition of emulsifiers and dispersants and, where water is used as the diluent, with or without an organic auxiliary solvent. Suitable auxiliaries are, essentially, solvents, for example aromatics, e.g. xylene and benzene, chloroaromatics, e.g. chlorobenzene, paraffins, e.g., petroleum fractions, alcohols, e.g. methanol and butanol, amines, e.g. ethanolamine, and dimethylformamide and water; carriers, for example natural rock powders, e.g. kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The fungicidal agents generally contain from 0.1 to 95, preferably from 0.5 to 90, wt% of active ingredient.

The application rates depend on the effect desired, and range from 0.1 to 3 kg of active ingredients per hectare, or more.

The novel compounds may also be used for protecting materials. The following wood- and paint-discoloring fungi, soft-rot and wood-destroying fungi, for instance, may be combatted with the agents according to the invention: *Pullularia* (*Aureobasidium*) *pullulans, Sclerophoma pityophila,* Ceratocystis spec., *Paecilomyces variotii,* Hormiscium spec., Stemphylium spec., *Phoma violacea, Cladosporium herbarum, Trichoderma viride, Chaetomium globosum, Humicola grisea, Merulius lacrimans, Coniophora puteana, Lentinus lepideus, Lenzites trabea, Polystictus versicolor, Stereum hirsutum,* and *Fomes annosus.*

For protecting materials, the novel active ingredients may be used as formulations, such as solutions, emulsions, pastes and oil dispersion. The formulations generally contain from 0.1 to 95, and preferably from 0.25 to 50, wt% of active ingredient. The application rates depend on the type of effect desired, and range from 0.5 to 8 g of active ingredient per $m^2$ of wood surface to be protected, or from 50 to 4,000 $g/m^3$ of wood. Paints contain from 0.5 to 5 wt% of active ingredient. To protect wood-base materials, the active ingredients are added to the adhesive as an emulsion, or admixture with it, in amounts of from 2 to 6 wt%. The active ingredients are applied by painting, spraying, atomizing, impregnation, or pressure-impregnation or diffusion. Water repellants may also be added to the oily wood preservatives to give water-repellant impregnation finishes. Examples of suitable substances are zinc stearate, aluminum stearate, and waxes. To achieve color effects, inorganic or organic pigments may be incorporated into the formulations.

The agents and the ready-to-use formulations made therefrom, e.g., solutions, emulsions, suspensions, powders, dusts, pastes or granules, are applied in known manner, for example by spraying, atomizing, dusting, scattering, seed-disinfecting, or watering.

In these application forms, the agents according to the invention may also be mixed and applied with other active ingredients, e.g., herbicides, insecticides, growth regulators, other fungicides and fertilizers. When mixed with other fungicides, the spectrum of fungicidal action is in many cases increased. With a number of these fungicidal mixtures, synergistic effects also occur, i.e., the effectiveness of the combination product is greater than the combined effects of the individual components.

Examples of fungicides which may be combined with the active ingredients according to the invention are as follows:

sulfur
dithiocarbamates and derivatives thereof, such as
ferric dimethyldithiocarbamate
zinc dimethyldithiocarbamate
manganese ethylenebisdithiocarbamate
zinc ethylenebisthiocarbamate
tetramethylthiuram disulfide
manganese-zinc ethylenediamine-bisdithiocarbamate
zinc-(N,N'-propylene-bisdithiocarbamate)
ammonia complex of zinc-(N,N'-ethylene)-bisdithiocarbamate and
N,N'-polyethylene-bis-(thiocarbamoyl)-disulfide
ammonia complex of zinc-(N,N'-propylene-bisdithiocarbamate) and
N,N'-polypropylene-bis-(thiocarbamoyl)-disulfide
nitro derivatives, such as
dinitro-(1-methylheptyl)-phenylcrotonate
2-sec-butyl-4,6-dinitrophenyl-3,5-dimethylacrylate
2-sec-butyl-4,6-dinitrophenylisopropylcarbonate
diisopropyl 5-nitroisophthalate
heterocyclic structures, such as
2-heptadecyl-2-imidazoline acetate
2,4-dichloro-6-(o-chloroanilino)-s-triazine
O,O-diethylphthalimidophosphorothionate
5-amino-1-[bis-(dimethylamino)-phosphynyl]-3-phenyl-1,2,4-triazole
2,3-dicyano-1,4-dithiaanthraquinone
2-thio-1,3-dithio-(4,5-b)-quinoxaline
methyl 1-(butylcarbamoyl)-2-benzimidazole carbamate
2-methoxycarbonylaminobenzimidazole
2-[furyl-(2)]-benzimidazole
2-[thiazolyl-(4)]-benzimidazole
N-(1,1,2,2-tetrachloroethylthio)-tetrahydrophthalimide
N-trichloromethylthiotetrahydrophthalimide
N-trichloromethylphthalimide
N-dichlorofluoromethylthio-N',N'-dimethyl-N-phenyl-sulfuric acid diamide
5-ethoxy-3-trichloromethyl-1,2,3-thiadiazole
2-thiocyanomethylthiobenzthiazole
1,4-dichloro-2,5-dimethoxybenzole
4-(2-chlorophenylhydrazono)-3-methyl-5-isoxazolone
pyridine-2-thio-1-oxide
8-hydroxyquinoline and its copper salt
2,3-dihydro-5-carboxanilido-6-methyl-1,4-oxathiin
2,3-dihydro-5-carboxanilido-6-methyl-1,4-oxathiin-4,4-dioxide
2-methyl-5,6-dihydro-4-H-pyran-3-carboxanilide
2-methyl-furan-3-carboxanilide
b 2,5-dimethyl-furan-3-carboxanilide
2,4,5-trimethyl-furan-3-carboxanilide
2,5-dimethyl-furan-3-carboxylic acid cyclohexylamide
N-cyclohexyl-N-methoxy-2,5-dimethyl-furan-3-carboxamide
2-methyl-benzoic acid anilide
2-iodobenzoic anilide
N-formyl-N-morpholine-2,2,2-trichloroethylacetal
piperazine-1,4-diylbis-(1-(2,2,2-trichloroethyl)-formamide
1-(3,4-dichloroanilino)-1-formylamino-2,2,2-trichlorethane
2,6-dimethyl-N-tridecyl-morpholine and its salts
2,6-dimethyl-N-cyclododecyl-morpholine and its salts
N-[3-(p-tert.-butylphenyl)-2-methylpropyl]-cis-2,6-dimethylmorpholine
N-[3-(p-tert.-butylphenyl)-2-methylpropyl]-piperidine
1-[2-(2,4-dichlorophenyl)-4-ethyl-1,3-dioxolan-2-yl-ethyl]-1-H-1,2,4-triazole
1-[2-(2,4-dichlorophenyl)-4-n-propyl-1,3-dioxolan-2-yl-ethyl]-1-H-1,2,4-triazole
N-(n-propyl)-N-(2,4,6-trichlorophenoxyethyl)-N'-imidazol-ylurea
1-(4-chlorophenoxy)-3,3-dimethyl-1-(1H-1,2,4-triazol-1-yl)-2-butanone
1-(4-chlorophenoxy)-3,3-dimethyl-1-(1H-1,2,4-triazol-1-yl)-2-butanol
alpha-(2-chlorophenyl)-alpha-(4-chlorophenyl)-5-pyrimidinemethanol
5-butyl-2-dimethylamino-4-hydroxy-6-methylpyrimidine
bis-(p-chlorophenyl)-3-pyridinemethanol
1,2-bis-(3-ethoxycarbonyl-2-thioureido)-benzene
1,2-bis-(3-methoxycarbonyl)-2-thioureido)-benzene
and various substances, such as
dodecylguanidine acetate
3-[2-(3,5-dimethyl-2-oxycyclohexyl)-2-hydroxyethyl]-glutarimide
hexachlorobenzene
D,L-methyl-N-(2,6-dimethylphenyl)-N-(2-furoyl)-alanate
methyl D,L-N-(2,6-dimethylphenyl)-N-(2-methoxyacetyl)-alanate
N-(2,6-dimethylphenyl)-N-chloroacetyl-D,L-2-aminobutyrolactone
methyl DL-N-(2,6-dimethylphenyl)-N-(phenylacetyl)-alanate
5-methyl-5-vinyl-3-(3,5-dichlorophenyl)-2,4-dioxo-1,3-oxazolidine
3-(3,5-dichlorophenyl)-5-methyl-5-methoxymethyl-1,3-oxazolidin-2,4-dione
3-(3,5-dichlorophenyl)-1-isopropyl-carbamoylhydantoin
N-(3,5-dichlorophenyl)-1,2-dimethyl-cyclopropane-1,2-dicarboximide.

To increase the spectrum of action and particularly to combat wood-destroying or wood- and paint-discoloring fungi, the novel active ingredients may be combined with the following active ingredients:
organotin compounds, such as tributyltin oxide and tributyltin benzoate
methylene bis-thiocyanate
alkyl dimethylbenzylammonium chloride
cetylpyridinium chloride
chlorinated phenols, such as tetrachlorophenol and pentachlorophenol
tetrachloroisophthalic acid dinitrile
2-halobenzoic acid anilide
N-cyclohexyl-N-methoxy-2,5-dimethylfuran-3-carboxamide N,N-dimethyl-N'-phenyl-(N'-fluorodichloromethylthio)-sulfamide
N-phenyl-N,N'-dimethyl-N'-fluorodichloromethylthiosulfonyl diamide
methyl benzimidazole-2-carbamate
2-thiocyanomethylthiobenzothiazole
copper naphthenate
copper-8-oxyquinoline
alkali and other metal salts of N'-hydroxy-N-cyclohexyldiazenium oxide.

For the following experiments, prior art fungicidal active ingredients were used for comparison purposes. viz., 1-(2,4-dichlorophenyl)-2-(imidazolyl)-ethan-1-ol (comparative compound A), disclosed in French Pat. No. 2,249,616, (2,4-dichlorophenyl)-1,2,4-triazol-1-yl methyl ketone (comparative compound B) and tert-butyl-1,2,4-triazol-1-yl methyl ketone (comparative agent C) disclosed in German Laid-Open Application No. DE-OS 24 31 407.

EXPERIMENT 1

Action on wheat mildew

Leaves of pot-grown wheat seedlings of the "Jubilar" variety were sprayed with aqueous liquors, the solids of which consisted of 80% (by weight) of active ingredient and 20% of emulsifier, and dusted, 24 hours after the sprayed-on layer had dried, with spores of wheat mildew (*Erysiphe graminis* var. *tritici*). The plants were then placed in a greenhouse at 20° to 22° C. and 75 to 80% relative humidity. The extent of mildew spread was determined after 7 days.

The results of the experiment show that novel active ingredients 1, 3, 4, 6 to 10, 16, 18, 24 and 38, applied for instance as 0.006 or 0.0015% suspensions, had a better fungicidal action (e.g., 90%) than prior art compounds A and C (e.g., 70%).

EXPERIMENT 2

Action on leaf rust of wheat

Leaves of pot-grown wheat seedlings of the "Jubilar" variety were dusted with spores of rust (*Puccinia recondita*). The pots were then placed in a high humidity (90–95%) chamber at from 20° to 22° C. for 24 hours. During this time, the spores germinated and the germ tubes enetrated into the leaf tissue. The infected plants were then sprayed to run-off with aqueous liquors, the solids comprising 80% of active ingredient and 20% of emulsifier. After the spray coating had dried, the test plants were set up in a greenhouse at from 20° to 22° C. and from 65 to 70% relative humidity. After 8 days, the degree of development of the rust fungi on the leaves was determined.

The results of this experiment show that novel active ingredients 1, 3, 4, 6 to 10, 16 to 18, 25, 38 and 90, applied for example as 0.025 or 0.06% suspensions, had a better fungicidal action (e.g., 97%) than prior art compounds A, B and C (e.g., 70%).

EXPERIMENT 3

Action on Botrytis cinerea in pimientos

Pimiento seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidial suspension of the fungus *Botrytis cinerea*, and placed at 22° to 24° C. in a chamber of high humidity. After 5 days, the disease had spread to such a great extent on the untreated plants that the necroses covered the major portion of the leaves.

The results of this experiment show that novel active ingredients 3, 7, 8, 10, 15, 17 to 19, 21, 29, 35 and 90, applied for instance as 0.05% suspensions, had a better fungicidal action (e.g., 97%) than prior art compounds A, B and C (e.g., 70%).

EXPERIMENT 4

Action on cucumber mildew

The leaves of pot-grown cucumber seedlings of the "Chinesische Schlange" variety were sprayed at the 2-leaf stage with a spore suspension of cucumber mildew (*Erysiphe cichoracearum*). After about 20 hours, the plants were sprayed to runoff with aqueous emulsions consisting (dry basis) of 80% of active ingredient and 20% of emulsifier. After the sprayed-on layer had dried, the plants were set up in the greenhouse at from 20° to 22° C. and a relative humidity of 70 to 80%. To assess the action of the novel compounds, the extent of fungus spread was determined after 21 days.

The results of this experiment show that novel active ingredients 6 to 10, 13, 15 to 21, 24 to 28, and 90, applied for example as 0.025% suspensions, had a very good fungicidal action (e.g., 97%).

EXPERIMENT 5

Action on soft-rot and mold fungi

The active ingredients were dissolved in acetone and added, in amounts of 40 ppm, to a liquid 50% malt extract agar. The agar was poured into Petri dishes and allowed to solidify. The fungicide-containing nutrient agar was then centrally inoculated with *Chaetomium globosum*, a fungus which causes mold and soft rot, and *Trichoderma viride*, a green wood mold. After the dishes had been incubated for 5 days at 25° C., the development of the fungus colonies on the nutrient medium was assessed against a control (no active ingredient added).

The results of this experiment show that novel active ingredients 7 to 10, applied for instance at a rate of 40 ppm, had a very good fungicidal action (e.g., 97%).

EXPERIMENT 6

Fungicidal action on wood-destroying fungi

To determine the activity on the wood-destroying fungi *Coniophora puteana* and *Polystictus versicolor*, pine sapwood blocks measuring 50×25×15 mm were coated at a rate of 100 g/m² of wood surface with oily wood preservative formulations containing 1% of active ingredient. After the treated blocks had been stored for 4 weeks, they where placed, together with untreaded blocks, in glass dishes containing the fungi *Coniophora puteana* or *Polystictus versicolor* in a nutrient agar. The dishes were then incubated in an atmospheric laboratory at 22° C. and a relative humidity of 70%. After 3 months, the fungus mycelium attaching to the blocks was removed and the blocks were dried. The degree of wood destruction was then ascertained.

The results obtained show that novel active ingredients 3, 4, 7, 8, 9 and 10, applied for example as 1% formulations, had a very good fungicidal action (e.g., 100%).

The following examples and directions illustrate the preparation of the novel compounds and their precursors.

EXAMPLE 1

(a) Preparation of the starting material 15.6 g of 1-(4-chlorophenyl)-cyclobutane-1-carboxylic acid, dissolved in 80 ml of absolute tetrahydrofuran, were added dropwise to 7.68 g of lithium aluminum hydride in 250 ml of absolute tetrahydrofuran at room temperature, under nitrogen. The mixture was stirred for 1 hour under reflux and for 12 hours at room temperature, after which it was hydrolyzed with ice water, acidified with 10% strength sulfuric acid and extracted with methylene chloride. The extract was dried and the solvent was evaporated to give 11.5 g of 1-(4-chlorophenyl)-1-hydroxymethylcyclobutane of melting point 53°–54° C. This was dissolved in 105 ml of pyridine in the absence of moisture, and 7.8 g of methanesulfonyl chloride were added dropwise at 0°–5° C. Stirring was continued for 2 hours at this temperature, after which the suspension was poured into ice water and extracted with methylene chloride, the combined organic phases were washed with water and dried, the solvent was removed and the product was recrystallized from cyclohexane. 5.1 g of [1-(4-chlorophenyl)-cyclobut-1-yl]-methyl methanesulfonate of melting point 66°–70° C. were obtained.

(b) Preparation of the end product 4.1 g of 1,2,4-triazole in 15 ml of N,N-dimethylformamide were added to 0.66 g of sodium hydride (80% strength dispersion in mineral oil) in 15 ml of N,N-dimethylformamide at room temperature, under nitrogen. The mixture was stirred for 30 minutes, after which 5.1 g of [1-(4-chlorophenyl)-cyclobut-1-yl]-methyl methanesulfonate in 15 ml of N,N-dimethylformamide were added dropwise, and the mixture was stirred for 24 hours at room temperature and for 12 hours at 100° C., then hydrolyzed with water and extracted with ethyl acetate. 2.6 g of 1-(4-chlorophenyl)-1-(1,2,4-triazol-1-ylmethyl)-cyclobutane of melting point 124°–125° C. were obtained.

EXAMPLE 2

(a) Preparation of the starting material 48 g of 4-phenylbenzaldehyde and 39.9 g of 4-chlorobenzyl cyanide were stirred with 3 g of sodium methylate in 400 ml of ethanol for 1 hour at 30° C. The precipitate formed was filtered off under suction and washed with a little isopropanol and then with petroleum ether. 82.5 g of Z-1-(4-chlorophenyl)-2-(4-biphenylyl)acrylonitrile of melting point 194°–198° C. were obtained.

34 g of potassium tert.-butylate were introduced, a little at a time, into a solution of 80 g of 1-(4-chlorophenyl)-2-(4-biphenylyl)-acrylonitrile and 80 g of trimethylsulfoxonium iodide in 750 ml of dimethyl sulfoxide, while cooling at 15° C. and under nitrogen. Stirring was continued for 1 hour at room temperature, after which the mixture was poured onto water and extracted with methylene chloride, the organic phase was washed with water and dried over magnesium sulfate, the solvent was evaporated off under reduced pressure and the residue was taken up in warm ethanol. 78.6 g of 1-(4-chlorophenyl)-2-(4-biphenylyl)-cyclopropyl cyanide of melting point 129°–131° C. crystallized from this solution.

75 g of this product were taken up in a mixture of 500 ml of diethyl ether and 100 ml of tetrahydrofuran, and 300 ml of a 1.2 molar solution of diisobutyl aluminum hydride in toluene were added dropwise at from 0° to 4° C., under nitrogen. The mixture was stirred for 1.5 hours at room temperature and then poured onto 2 liters of 10% strength aqueous tartaric acid solution, a further 2 liters of diethyl ether were added, and the organic phase was separated off, washed with water and dried over magnesium sulfate. On evaporating down the solution, a precipitate formed; this was filtered off under suction, washed with water and a little petroleum ether and recrystallized from methanol to give 73 g of 1-(4-chlorophenyl)-2-(4-biphenylyl)-cyclopropylcarbaldehyde of melting point 188°–190° C.

73 g of this product in a mixture of 1 liter of methanol and 1 liter of methylene chloride were stirred with 6 g of sodium borohydride for 2 hours, after which the solvent was evaporated off under reduced pressure, the residue was taken up in methylene chloride, the solution was washed with water, dried over magnesium sulfate and evaporated to dryness, and the residue was recrystallized from toluene to give 68 g of 1-(4-chlorophenyl)-1-hydroxymethyl-2-(4-biphenylyl)-cyclopropane of melting point 168°–170° C.

(b) Preparation of the end product 4.8 ml of methanesulfonyl chloride in 15 ml of methylene chloride were added dropwise to 16.5 g of 1-(4-chlorophenyl)-1-hydroxymethyl-2-(4-biphenylyl)-cyclopropane in 150 ml of methylene chloride and 8.6 ml of triethylamine at 20° C. The mixture was stirred for 2 hours at room temperature, after which it was washed with dilute sodium bicarbonate solution and then with water and dried over magnesium sulfate, and the solvent was distilled off under reduced pressure.

The solid residue was taken up in 50 ml of dimethyl sulfoxide, 1 g of potassium iodide was added and the mixture was added dropwise, at room temperature and under nitrogen, to a solution prepared from 4.1 g of imidazole and 2.4 g of sodium hydride (80% strength dispersion in mineral oil) in 150 ml of dimethylformamide at 15° C. Stirring was carried out for 24 hours at room temperature, after which the reaction solution was poured into water and extracted with methylene chloride, the organic phase was washed with water and dried over magnesium sulfate, and the solvent was evaporated off to give a syrup. This was taken up in warm acetone, and a saturated solution of hydrogen chloride in diisopropyl ether was added. 14.5 g of 1-(4-chlorophenyl)-1-(imidazol-1-ylmethyl)-2-(4-biphenylyl)-cyclopropane crystallized out as the monohydrochloride; mp. 212°–214° C.

The compounds listed in Tables 1 and 2 can be prepared, or were prepared, by a procedure similar to that described in Examples 1 and 2:

TABLE 1

| | (D = E = hydrogen) | | | | | | |
|---|---|---|---|---|---|---|---|
| Example | A | B | m | n | Z | Base/salt | Mp. [°C.] |
| 3 | 4-Cl—C$_6$H$_4$ | 2,4-Cl$_2$—C$_6$H$_3$ | 1 | 0 | CH | .HCl | 228–234 |
| 4 | 4-Cl—C$_6$H$_4$ | 2,4-Cl$_2$—C$_6$H$_3$ | 1 | 0 | N | .HCl | 207–213 |

TABLE 1-continued
(D = E = hydrogen)

| Example | A | B | m | n | Z | Base/salt | Mp. [°C.] |
|---|---|---|---|---|---|---|---|
| 5 | $C_6H_5$ | $4\text{-}Cl\text{-}C_6H_4$ | 1 | 0 | CH | | 56-57.5 |
| 6 | $C_6H_5$ | $4\text{-}Cl\text{-}C_6H_4$ | 1 | 0 | N | | 94-96 |
| 7 | $4\text{-}Cl\text{-}C_6H_4$ | $C_6H_5$ | 1 | 0 | CH | .HCl | 221-228 |
| 8 | $4\text{-}Cl\text{-}C_6H_4$ | $C_6H_5$ | 1 | 0 | N | .HCl | 163-168 |
| 9 | $4\text{-}Cl\text{-}C_6H_4$ | $4\text{-}Cl\text{-}C_6H_4$ | 1 | 0 | CH | | 86-88 |
| 10 | $4\text{-}Cl\text{-}C_6H_4$ | $4\text{-}Cl\text{-}C_6H_4$ | 1 | 0 | N | | 86-88 |
| 11 | $3,4\text{-}(OCH_3)_2\text{-}C_6H_3$ | $2,4\text{-}Cl_2\text{-}C_6H_3$ | 1 | 0 | N | | 117 |
| 12 | $3,4\text{-}(OCH_3)_2\text{-}C_6H_3$ | $2,4\text{-}Cl_2\text{-}C_6H_3$ | 1 | 0 | CH | | 121 |
| 13 | $3,4\text{-}(OCH_3)_2\text{-}C_6H_3$ | $4\text{-}Cl\text{-}C_6H_4$ | 1 | 0 | N | | 118-120 |
| 14 | $3,4\text{-}(OCH_3)_2\text{-}C_6H_3$ | $4\text{-}Cl\text{-}C_6H_4$ | 1 | 0 | CH | | 92-116 |
| 15 | $4\text{-}Cl\text{-}C_6H_4$ | $3\text{-}CF_3\text{-}C_6H_4$ | 1 | 0 | CH | | 219-226 |
| 16 | $4\text{-}Cl\text{-}C_6H_4$ | $3\text{-}CF_3\text{-}C_6H_4$ | 1 | 0 | N | .HCl | 126-128 |
| 17 | $4\text{-}Br\text{-}C_6H_4$ | $4\text{-}CF_3\text{-}C_6H_4$ | 1 | 0 | CH | .HCl | 159-162 |
| 18 | $4\text{-}Br\text{-}C_6H_4$ | $4\text{-}F\text{-}C_6H_4$ | 1 | 0 | N | .HCl | 195-200 |
| 19 | $4\text{-}Cl\text{-}C_6H_4$ | $3\text{-}(O\text{-}C_6H_5)\text{-}C_6H_4$ | 1 | 0 | CH | .HCl | 220-225 |
| 20 | $4\text{-}Cl\text{-}C_6H_4$ | $3\text{-}(O\text{-}C_6H_5)\text{-}C_6H_4$ | 1 | 0 | N | .HCl | 168-171 |
| 21 | $1\text{-}C_{10}H_7$ | $4\text{-}Cl\text{-}C_6H_4$ | 1 | 0 | CH | $.(CO_2H)_2$ | 185-188 |
| 22 | $1\text{-}C_{10}H_7$ | $4\text{-}Cl\text{-}C_6H_4$ | 1 | 0 | CH | .HCl | 168-170 |
| 23 | $C_6H_5$ | H | 1 | 0 | N | | 31-34 |
| 24 | $4\text{-}Cl\text{-}C_6H_4$ | H | 1 | 0 | N | .HCl | 145-153 |
| 25 | $4\text{-}Cl\text{-}C_6H_4$ | $4\text{-}C_6H_5\text{-}C_6H_4$ | 1 | 0 | N | .HCl | 174-180 |
| 26 | $4\text{-}Cl\text{-}C_6H_4$ | $4\text{-}C(CH_3)_2\text{-}C_6H_4$ | 1 | 0 | N | .HCl | 135-140 |
| 27 | $4\text{-}CH_3\text{-}C_6H_4$ | $4\text{-}Cl\text{-}C_6H_4$ | 1 | 0 | N | .HCl | 160-175 |
| 28 | $4\text{-}Cl\text{-}C_6H_4$ | H | 1 | 0 | CH | .HCl | 199-204 |
| 29 | $4\text{-}CH_3\text{-}C_6H_4$ | $4\text{-}Cl\text{-}C_6H_4$ | 1 | 0 | CH | | 84-86 |
| 30 | $4\text{-}Cl\text{-}C_6H_4$ | $4\text{-}C(CH_3)_3\text{-}C_6H_4$ | 1 | 0 | CH | | 98-99 |
| 31 | $4\text{-}Cl\text{-}C_6H_4$ | $3,4\text{-}Cl_2\text{-}C_6H_3$ | 1 | 0 | CH | .HCl | 210-215 |
| 32 | $4\text{-}Cl\text{-}C_6H_4$ | $3,4\text{-}Cl_2\text{-}C_6H_3$ | 1 | 0 | N | .HCl | 145-154 |
| 33 | $4\text{-}Cl\text{-}C_6H_4$ | $2\text{-}Cl\text{-}C_6H_4$ | 1 | 0 | CH | .HCl | 258-269 |
| 34 | $C_6H_5$ | $2\text{-}Cl\text{-}C_6H_4$ | 1 | 0 | CH | .HCl | 246-256 |
| 35 | $C_6H_5$ | $4\text{-}Cl\text{-}C_6H_4$ | 1 | 0 | N | .HCl | 183-189 |
| 36 | $4\text{-}Cl\text{-}C_6H_4$ | $2\text{-}Cl\text{-}C_6H_4$ | 1 | 0 | N | .HCl | 177-180 |
| 37 | $4\text{-}Cl\text{-}C_6H_4$ | H | 2 | 0 | CH | | |
| 38 | $4\text{-}Cl\text{-}C_6H_4$ | H | 3 | 0 | N | | 102-103 |
| 39 | $4\text{-}Cl\text{-}C_6H_4$ | H | 3 | 0 | CH | | |
| 40 | $2,4\text{-}Cl_2\text{-}C_6H_3$ | H | 2 | 0 | N | | |
| 41 | $2,4\text{-}Cl_2\text{-}C_6H_3$ | H | 2 | 0 | CH | | |
| 42 | $4\text{-}Cl\text{-}C_6H_4$ | H | 2 | 2 | N | | 90-92 |
| 43 | $4\text{-}Cl\text{-}C_6H_4$ | $CH_3$ | 2 | 1 | N | | 162-165* |
| 44 | $4\text{-}Cl\text{-}C_6H_4$ | $CH_3$ | 2 | 1 | CH | .HCl | 179-184* |
| 45 | $2,4\text{-}Cl_2\text{-}C_6H_3$ | $C_2H_5$ | 2 | 1 | N | | |
| 46 | $4\text{-}Cl\text{-}C_6H_4$ | $n\text{-}C_3H_7$ | 2 | 1 | N | | |
| 47 | $2,4\text{-}Cl_2\text{-}C_6H_3$ | $n\text{-}C_3H_7$ | 2 | 1 | N | | |
| 48 | $2,4\text{-}Cl_2\text{-}C_6H_3$ | $n\text{-}C_4H_9$ | 2 | 1 | N | | |
| 49 | $2,4\text{-}Cl_2\text{-}C_6H_3$ | $n\text{-}C_4H_9$ | 2 | 1 | CH | | |
| 50 | $4\text{-}Cl\text{-}C_6H_4$ | $C_6H_5$ | 2 | 1 | N | .HCl | 163-168** |
| 51 | $4\text{-}Cl\text{-}C_6H_4$ | $C_6H_5$ | 2 | 1 | CH | .HCl | 198-200** |
| 52 | $2,4\text{-}Cl_2\text{-}C_6H_3$ | $C_6H_5$ | 2 | 2 | N | | |
| 53 | $2,4\text{-}Cl_2\text{-}C_6H_3$ | $C_6H_5$ | 2 | 2 | CH | | |
| 54 | $4\text{-}Cl\text{-}C_6H_4$ | $n\text{-}C_3H_7$ | 2 | 1 | N | | |
| 55 | $2,4\text{-}Cl_2\text{-}C_6H_3$ | $n\text{-}C_3H_7$ | 4 | 1 | N | | |
| 56 | 3-Furanyl | $4\text{-}Cl\text{-}C_6H_4$ | 1 | 0 | N | | |
| 57 | 3-Furanyl | $4\text{-}Cl\text{-}C_6H_4$ | 1 | 0 | CH | | |
| 58 | 3-Thienyl | $4\text{-}Cl\text{-}C_6H_4$ | 1 | 0 | N | | resin oil |
| 59 | 3-Thienyl | $4\text{-}Cl\text{-}C_6H_4$ | 1 | 0 | CH | | oil |
| 59a | 3-Thienyl | $4\text{-}Cl\text{-}C_6H_4$ | 1 | 0 | CH | ½ $CuCl_2$ | 121 (decomposition) |
| 60 | 3-Pyridyl | $4\text{-}Cl\text{-}C_6H_4$ | 1 | 0 | N | | |
| 61 | 3-Pyridyl | $4\text{-}Cl\text{-}C_6H_4$ | 1 | 0 | CH | | |
| 62 | $4\text{-}Br\text{-}C_6H_4$ | $4\text{-}Cl\text{-}C_6H_4$ | 1 | 0 | N | .HCl | 205-208 |
| 63 | $4\text{-}Br\text{-}C_6H_4$ | $4\text{-}Cl\text{-}C_6H_4$ | 1 | 0 | CH | | resin |
| 64 | $4\text{-}Cl\text{-}C_6H_4$ | $4\text{-}F\text{-}C_6H_4$ | 1 | 0 | N | | 84-92 |
| 65 | $4\text{-}Cl\text{-}C_6H_4$ | $4\text{-}F\text{-}C_6H_4$ | 1 | 0 | CH | | resin |
| 66 | $4\text{-}Br\text{-}C_6H_4$ | $C_6H_5$ | 1 | 0 | N | .HCl | 164-170 |
| 67 | $4\text{-}Br\text{-}C_6H_4$ | $C_6H_5$ | 1 | 0 | CH | | |
| 68 | $4\text{-}Cl\text{-}C_6H_4$ | $CF_3$ | 1 | 0 | CH | | |
| 69 | $4\text{-}Cl\text{-}C_6H_4$ | $CF_3$ | 1 | 0 | N | | |
| 70 | $4\text{-}Cl\text{-}C_6H_4$ | $CCl_3$ | 1 | 0 | CH | | |
| 71 | $4\text{-}Cl\text{-}C_6H_4$ | $CCl_3$ | 1 | 0 | N | | |
| 72 | $4\text{-}Cl\text{-}C_6H_4$ | $4\text{-}(S\text{-}C_6H_5)\text{-}C_6H_4$ | 1 | 0 | CH | | |
| 73 | $4\text{-}Cl\text{-}C_6H_4$ | $4\text{-}(S\text{-}C_6H_5)\text{-}C_6H_4$ | 1 | 0 | N | | |
| 74 | $4\text{-}(S\text{-}C_6H_5)\text{-}C_6H_4$ | $4\text{-}Cl\text{-}C_6H_4$ | 1 | 0 | N | | |
| 75 | $4\text{-}(S\text{-}C_6H_5)\text{-}C_6H_4$ | $2,4\text{-}Cl_2\text{-}C_6H_3$ | 1 | 0 | N | | |
| 76 | $2,4\text{-}Cl_2\text{-}C_6H_3$ | 2-Furanyl | 1 | 0 | CH | .HCl | 229-239 |
| 77 | $2,4\text{-}Cl_2\text{-}C_6H_3$ | 2-Furanyl | 1 | 0 | N | .HCl | 155-165 |
| 78 | $4\text{-}Cl\text{-}C_6H_4$ | $3\text{-}Cl\text{-}C_6H_4$ | 1 | 0 | CH | .HCl | 210-220 |
| 79 | $4\text{-}Cl\text{-}C_6H_4$ | $3\text{-}Cl\text{-}C_6H_4$ | 1 | 0 | N | .HCl | 152-158 |
| 80 | $C_6H_5$ | $2,6\text{-}Cl_2\text{-}C_6H_3$ | 1 | 0 | CH | .HCl | 292-294 |
| 81 | $C_6H_5$ | $2,6\text{-}Cl_2\text{-}C_6H_3$ | 1 | 0 | N | .HCl | 180-182 |
| 82 | $4\text{-}Cl\text{-}C_6H_4$ | $C(CH_3)_3$ | 1 | 0 | CH | .HCl | 246-250 |
| 83 | $4\text{-}Cl\text{-}C_6H_4$ | $C(CH_3)_3$ | 1 | 0 | N | .HCl | 188-192 |

TABLE 1-continued

| | | (D = E = hydrogen) | | | | | |
|---|---|---|---|---|---|---|---|
| Example | A | B | m | n | Z | Base/salt | Mp. [°C.] |
| 84 | 4-Cl—C$_6$H$_4$ | CH$_3$ | 1 | 0 | CH | | |
| 85 | 4-Cl—C$_6$H$_4$ | CH$_3$ | 1 | 0 | N | | |
| 86 | 4-Cl—C$_6$H$_4$ | 2-Thienyl | 1 | 0 | N | .HCl | 165–185 |
| 87 | 4-Cl—C$_6$H$_4$ | 3-Thienyl | 1 | 0 | N | | |
| 88 | 4-Cl—C$_6$H$_4$ | 2-Thienyl | 1 | 0 | CH | .HCl | 223–226 |
| 89 | 4-Cl—C$_6$H$_4$ | 3-Thienyl | 1 | 0 | CH | | |
| 90 | 4-Cl—C$_6$H$_4$ | 2-Furanyl | 1 | 0 | CH | .HCl | 211–215 |
| 91 | 4-Cl—C$_6$H$_4$ | 2-Furanyl | 1 | 0 | N | .HCl | 135–145 |
| 92 | 4-Cl—C$_6$H$_4$ | 4-C$_6$H$_5$—C$_6$H$_4$ | 1 | 0 | CH | .HCl | 212–214 |

*1:1 diastereomer pair
**cis-diastereomer

TABLE 2

| Example | A | B | D | E | m | n | Z | Base/salt | Mp. [°C.] |
|---|---|---|---|---|---|---|---|---|---|
| 93 | H | C$_6$H$_5$ | Cl | Cl | 1 | 0 | N | .HCl | 140–144 |
| 94 | H | 4-Cl—C$_6$H$_4$ | Cl | Cl | 1 | 0 | N | .HCl | 161–168 |
| 95 | 4-Cl—C$_6$H$_4$ | C$_6$H$_5$ | Cl | Cl | 1 | 0 | CH | | |
| 96 | 4-Cl—C$_6$H$_4$ | C$_6$H$_5$ | Cl | Cl | 1 | 0 | N | | |
| 97 | H | 4-Cl—C$_6$H$_4$ | F | F | 1 | 0 | N | | |
| 98 | H | 4-Cl—C$_6$H$_4$ | F | F | 1 | 0 | CH | | |
| 99 | 4-F—C$_6$H$_4$ | 2,4-Cl$_2$—C$_6$H$_4$ | H | H | 1 | 0 | CH | .HCl | 194–197 |
| 100 | 4-F—C$_6$H$_4$ | 2,4-Cl$_2$—C$_6$H$_4$ | H | H | 1 | 0 | N | .HCl | 170–179 |
| 101 | C$_6$H$_5$ | 4-Cl—C$_6$H$_4$ | F | F | 1 | 0 | N | | |
| 102 | C$_6$H$_5$ | H | F | F | 1 | 0 | CH | | |
| 103 | C$_6$H$_5$ | H | F | F | 1 | 0 | N | | |
| 104 | 4-Cl—C$_6$H$_4$ | H | F | F | 1 | 0 | CH | | |
| 105 | 4-Cl—C$_6$H$_4$ | H | F | F | 1 | 0 | N | | |
| 106 | 4-Cl—C$_6$H$_4$ | H | H | Br | 1 | 0 | CH | | |
| 107 | 4-Cl—C$_6$H$_4$ | H | H | Br | 1 | 0 | N | | |
| 108 | 4-Cl—C$_6$H$_4$ | H | Cl | Cl | 1 | 0 | CH | | |
| 109 | 4-Cl—C$_6$H$_4$ | H | Cl | Cl | 1 | 0 | N | | |
| 110 | C$_6$H$_5$ | H | Cl | Cl | 1 | 0 | CH | | |
| 111 | C$_6$H$_5$ | H | Cl | Cl | 1 | o | N | | |

Pharmaceutical formulations

EXAMPLE A

Tablet containing 250 mg of active compound
Composition for 1,000 tablets:
Active compound of Example No. 3: 250 g;
Potato starch: 100 g;
Lactose: 50 g;
4% strength gelatine solution: 45 g;
Talc: 10 g.

Preparation: The finely powdered active compound, potato starch and lactose are mixed, and the mixture is moistened thoroughly with about 45 g of 4% strength gelatine solution, finely granulated and dried. The dry granules are passed through a sieve and mixed with 10 g of talc, and the mixture is converted to tablets on a rotary tableting press. The tablets are introduced into polypropylene containers which can be tightly closed.

EXAMPLE B

Cream containing 1% of active compound
Active compound of Example No. 3: 1.0 g;
Glycerol monostearate: 10.0 g;
Cetyl alcohol: 4.0 g;
Polyethylene glycol-400 stearate: 10.0 g;
Polyethylene glycol sorbitan monostearate: 10.0 g;
Propylene glycol: 6.0 g;
Methyl p-hydroxybenzoate: 0.2 g;
Demineralized water to make up to 100.0 g.

Preparation:

The very finely powdered active compound is suspended in propylene glycol, and the suspension is stirred into a melt comprising glycerol monostearate, cetyl alcohol, polyethylene glycol-400 stearate and polyethylene glycol sorbitan monostearate, the melt having been heated to 65° C. beforehand. A solution, at 70° C., of methyl p-hydroxybenzoate in water is emulsified in this mixture. After the cream has cooled, it is homogenized in a colloid mill and introduced into tubes.

EXAMPLE C

Powder containing 1% of active compound
Active compound of Example No. 3: 1.0 g;
Zinc oxide: 10.0 g;
Magnesium oxide: 10.0 g;
Finely divided silicon dioxide: 2.5 g;
Magnesium stearate: 1.0 g;
Talc: 75.5.

Preparation:

The active compound is micronized in an air-jet mill, and is then mixed with the other components to give a homogeneous mixture. The latter is forced through a sieve (mesh size No. 7) and then introduced into polyethylene containers having a dusting attachment.

EXAMPLE I 20 parts by weight of the compound of Example 2 are mixed thoroughly with 3 parts by weight of sodium diisobutylnaphthalenesulfonate, 17 parts by weight of the sodium salt of a ligninsulfonic acid obtained from a sulfite waste liquor, and 60 parts by weight of pulverulent silica gel, and the mixture is milled in a hammer mill. A spray liquor is obtained by finely dispersing the mixture in water.

EXAMPLE II 3 parts by weight of the compound of Example 38 are mixed intimately with 97 parts by weight of finely divided kaolin. In this manner, a dusting agent which contains 3% by weight of the active compound is obtained.

EXAMPLE III 30 parts by weight of the compound of Example 4 are mixed intimately with 92 parts by weight of pulverulent silica gel, onto the surface of which 8 parts by weight of paraffin oil have been sprayed. In this manner, an active compound formulation having good adhesion is obtained.

EXAMPLE IV 40 parts by weight of the compound of Example 7 are mixed intimately with 10 parts of the sodium salt of a phenolsulfonic acid/urea/formaldehyde condensate, 2 parts of silica gel and 48 parts of water to give a stable aqueous dispersion. Dilution with water gives an aqueous dispersion.

EXAMPLE V 20 parts of the compound of Example 9 are mixed intimately with 2 parts of calcium dodecylbenzenesulfonate, 8 parts of a fatty alcohol polyglycol ether, 2 parts of the sodium salt of a phenolsulfonic acid/urea formaldehyde condensate and 68 parts of a paraffinic mineral oil to give a stable oily dispersion.

EXAMPLE VI 90 parts by weight of the compound of Example 17 are mixed with 10 parts by weight of N-methyl-alpha-pyrrolidone, and the resulting solution can be used in the form of very fine drops.

EXAMPLE VII 20 parts by weight of the compound of Example 4 are dissolved in a mixture consisting of 80 parts by weight of xylene, 10 parts by weight of an adduct of 8-10 moles of ethylene oxide with 1 mole of oleic acid N-monoethanolamide, 5 parts by weight of calcium dodecylbenzenesulfonate and 5 parts by weight of an adduct of 40 moles of ethylene oxide with 1 mole of castor oil. When the solution is poured into water and finely dispersed therein, an aqueous dispersion is obtained.

EXAMPLE VIII 20 parts by weight of the compound of Example 9 are dissolved in a mixture consisting of 40 parts by weight of cyclohexanone, 30 parts by weight of isobutanol, 20 parts by weight of an adduct of 7 moles of ethylene oxide and 1 mole of isooctylphenol, and 10 parts by weight of an adduct of 40 moles of ethylene oxide with 1 mole of castor oil. When the solution is poured into water and finely dispersed therein, an aqueous dispersion is obtained.

EXAMPLE IX 10 parts by weight of the compound of Example 12, 20 parts by weight of polyoxyethylene sorbitan monolaurate, 20 parts by weight of methanol and 50 parts by weight of water are stirred together to give a solution containing 10% by weight of the active compound. More dilute solutions can be prepared by adding further amounts of water.

EXAMPLE X

To prepare a solvent-containing wood preservative which contains 1% of active compound, first 1 part by weight of the compound of Example 3 is dissolved, with slight heating, in 55 parts of a gasoline fraction having a high aromatics content, and then 10 parts of an alkyd resin are added and the solution is made up to 100 parts with mineral spirit at room temperature.

Solvent-containing wood preservatives which contain as much as 5% by weight of active compound can be prepared by procedures similar to those described in Examples I to X.

We claim:

1. An azolylmethylcycloalkane of the formula I

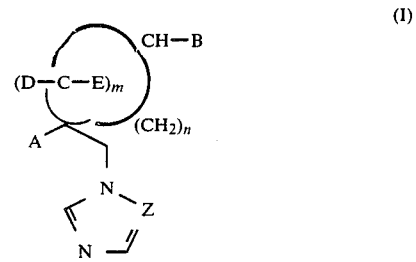

where A and B are identical or different and are each naphthyl, furanyl, thienyl, pyridyl, biphenyl or phenyl, where the phenyl radical can be substituted by halogen, nitro, alkyl, alkoxy or haloalkyl, each of 1 to 4 carbon atoms, phenoxy or phenylsulfenyl, D and E are identical or different and are each hydrogen or halogen, Z is CH or N, m is 1, 2 or 4 and n is 0 and its addition salts with acids, and its metal complexes.

2. An azolylmethylcyclopropane of the formula I as defined in claim 1, wherein D and E are each hydrogen and m is 1.

3. A fungicidal composition which contains an effective amount of an azolylmethylcycloalkane as defined in claim 1 and inert additives.

4. A method of controlling fungi, wherein an effective amount of an azolylmethylcycloalkane of the formula I as defined in claim 1 is allowed to act on the fungi or on materials, areas, plants or seeds threatened by fungal infestation.

5. A therapeutic composition for treating mycoses comprising a pharmaceutical excipient and an effective amount of a compound of the formula I as defined in claim 1.

6. The method of treating mycoses in a patient suffering therefrom, which comprises administering an effective amount of a compound of the formula I as defined in claim 1.

7. An azolymethylcycloalkane of the formula I

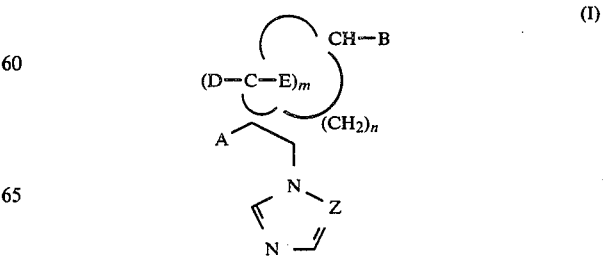

wherein A is unsubstituted or halogen-substituted alkyl of 1 to 4 carbon atoms, naphthyl, furanyl, thienyl, pyridyl, biphenyl or phenyl, where the phenyl radical can be substituted by halogen, nitro, alkyl, alkoxy or haloalkyl, each of 1 to 4 carbon atoms, phenoxy or phenylsulfenyl, B is selected from the group consisting of naphthyl, furanyl, thienyl, pyridyl, unsubstituted phenyl and phenyl substituted by halogen, nitro, alkyl of 1-4 carbons, alkoxy of 1-4 carbons, haloalkyl of 1-4 carbons, phenoxy or phenylsulfenyl, D and E are identical or different and are each hydrogen or halogen, Z is CH or N, m is 1, 2 or 4 and n is 0, and its addition salts with the acids, and its metal complexes.

* * * * *